US012807803B2

(12) United States Patent
Verswyvel et al.

(10) Patent No.: US 12,807,803 B2
(45) Date of Patent: Nov. 24, 2026

(54) STYRENE BUTADIENE BLOCK COPOLYMER COMPOSITIONS FOR MEDICAL DEVICES

(71) Applicant: INEOS STYROLUTION GROUP GMBH, Frankfurt am Main (DE)

(72) Inventors: Michiel Verswyvel, Mechelen (BE); Norbert Niessner, Friedelsheim (DE); Florian Jochum, Heidesheim (DE); Bernd Elbert, Harsefeld (DE)

(73) Assignee: INEOS STYROLUTION GROUP GMBH, Frankfurt am Main (DE)

( * ) Notice: Subject to any disclaimer, the term of this patent is extended or adjusted under 35 U.S.C. 154(b) by 902 days.

(21) Appl. No.: 17/768,360

(22) PCT Filed: Oct. 12, 2020

(86) PCT No.: PCT/EP2020/078607
§ 371 (c)(1),
(2) Date: Apr. 12, 2022

(87) PCT Pub. No.: WO2021/074075
PCT Pub. Date: Apr. 22, 2021

(65) Prior Publication Data

US 2024/0026147 A1 Jan. 25, 2024

(30) Foreign Application Priority Data

Oct. 14, 2019 (EP) .................................... 19203041

(51) Int. Cl.

| | |
|---|---|
| ***C08L 53/02*** | (2006.01) |
| ***A61M 5/14*** | (2006.01) |
| ***C08F 297/04*** | (2006.01) |

(52) U.S. Cl.
CPC ............ *C08L 53/02* (2013.01); *A61M 5/1411* (2013.01); *C08F 297/044* (2013.01); *C08L 2205/025* (2013.01)

(58) Field of Classification Search
CPC ......... C08L 53/00; C08L 53/02; C09J 153/00; C09J 153/02; C09D 153/00; C09D 153/02; C08F 293/00; C08F 293/005; C08F 297/00; C08F 97/04; C08F 297/042; C08F 297/044
See application file for complete search history.

(56) References Cited

U.S. PATENT DOCUMENTS

| | | | | |
|---|---|---|---|---|
| 5,331,048 A * | 7/1994 | Hasselbring | ............ C08L 53/02 525/98 | |
| 6,031,054 A | 2/2000 | Takai | | |
| 6,177,517 B1 | 1/2001 | Guentherberg | | |
| 6,197,889 B1 | 3/2001 | Knoll | | |
| 2009/0286918 A1 | 11/2009 | Stewart | | |
| 2010/0304067 A1 | 12/2010 | Knoll | | |
| 2012/0061287 A1 | 3/2012 | Knoll | | |

FOREIGN PATENT DOCUMENTS

| | | | | |
|---|---|---|---|---|
| CN | 202289064 U | 7/2012 | | |
| EP | 0612672 A1 * | 8/1994 | ............. C08L 53/02 | |
| WO | 95/35335 A1 | 12/1995 | | |
| WO | 96/20248 A1 | 7/1996 | | |
| WO | 96/24634 A1 | 8/1996 | | |
| WO | 97/40079 A1 | 10/1997 | | |
| WO | 01/94466 A1 | 12/2001 | | |
| WO | 2008/000623 A1 | 1/2008 | | |
| WO | 2009/037115 A1 | 3/2009 | | |
| WO | 2010/072596 A1 | 7/2010 | | |
| WO | 2012/037462 A1 | 3/2012 | | |
| WO | 2016/034609 A1 | 3/2016 | | |
| WO | 2018/166950 A1 | 9/2018 | | |
| WO | 2018/166958 A1 | 9/2018 | | |

* cited by examiner

*Primary Examiner* — Jeffrey S Lenihan

(74) *Attorney, Agent, or Firm* — RAPHAEL BELLUM PLLC

(57) ABSTRACT

The present invention relates to transparent and flexible styrene butadiene copolymer compositions having high softness and temperature resistance as well as good processability, and the process for their preparation. Further, the invention is directed to shaped articles produced from the inventive polymer composition, and the use of said polymer composition for preparing moldings, in particular for medical applications, in particular medical drip chambers.

14 Claims, No Drawings

STYRENE BUTADIENE BLOCK COPOLYMER COMPOSITIONS FOR MEDICAL DEVICES

The present invention relates to transparent and flexible styrene butadiene copolymer compositions having high softness and temperature resistance as well as good processability, and the process for their preparation. Further, the present invention relates to shaped articles produced from these (SBC) polymer compositions, and the use of said polymer compositions for preparing moldings, in particular for medical applications, in particular medical drip chambers.

Transparent and flexible medical devices, used to transport any variety of liquids during medical procedures, such as medical tubes and bags, are frequently made from plasticized polyvinylchloride (PVC). However, the use of plasticized polyvinylchloride has several disadvantages, in particular migration of harmful plasticizers from the PVC into the human body and undesired environmental impact during disposal of PVC-based waste.

Several polymer materials have been developed as alternative material to plasticized PVC. Often these polymer materials do not have all physical and mechanical properties that are required for the certain medical application. Typical, suitable polymer materials are flexible, transparent and elastic and exhibit sufficient thermal stability, e.g. desired for steam sterilization of the medical devices. Another requirement for the polymer materials is the good processability as medical devices are often produced in large quantities as they are produced for single use application due to public health safety.

For example WO 2001/94466 and WO 2012/037462 describe flexible medical tubes made from a composition containing a polyolefin, such as polypropylene, and a styrene-butadiene block copolymer.

Documents WO 2018/166958 and WO 2018/166950 describe polymer compositions comprising a star-shaped styrene butadiene copolymer and a plasticizer and their use for medical applications, such as medical tubings and bags. The document WO 2016/034609 proposes polymer blends comprising different styrene butadiene copolymers, wherein the blend should exhibit high transparency, good thermoforming behavior and improved multi-axial toughness.

WO 1996/24634 describes medical molded parts, such as a component for perfusion or transfusion systems. The medical part is made of a polymer mixture containing a rubber-elastic block copolymer and optionally another thermoplastic polymer.

Modern injection molding machines for the production of medical devices, such as drip chambers, provide large quantities and thus have an increasing amount of cavities. Thus, it is necessary to provide polymer compositions having excellent processability, such as high melt flow rate. In particular, an optimized melt flow rate is necessary in order to ensure that all cavities are filed without defects. In order to obtain good demolding properties, typically a demolding agent is added to the thermoplastic polymer composition. Typically, the addition of a demolding agent decrease the heat stability, e.g. lower the Vicat temperature. However, sufficient heat stability is necessary for several medical applications, e.g. for sterilization and for fast demolding during processing.

Furthermore, the medical devices should be soft, suitable for easy squeezing and deformation and, as a consequence, they should exhibit a low Shore D hardness. Therefore, plasticizers are very often added which typically impact the heat stability, and transparency negatively. Therefore, it is desired to avoid or reduce the use of plasticizers. Additionally, it is necessary that the medical device comes to its original shape very quickly after deformation, e.g. after squeezing. The medical devices should exhibit a high flexibility/resilience. These conflicting features require a thorough optimization and balance of properties.

It is one object of the present invention to provide polymer compositions that can be advantageously used for transparent, flexible medical devices, such as drip chambers, and that have such balance of properties as described above within given target values. In particular the polymer compositions should have improved thermoforming behavior suitable for production of large quantities, without loss in other properties as described above.

It was surprisingly found that this balance of properties including improved processability and thermoforming behavior is achieved by the polymer composition according to the invention comprising a defined vinyl aromatic hydrocarbon/conjugated diene copolymer, in particular a styrene butadiene block copolymer. In particular, it has been found that an optimized melt flow rate, in particular of more than 25 $cm^3$/10 min, preferably in the range of 25 to 40 $cm^3$/10 min (ISO 1133-1:2011, 200° C., 5 kg), is necessary in order to ensure that all cavities are filed without defects during the injection molding process.

Preferably, the polymer compositions according to the invention do not need any plasticizer and are free of PVC.

The present invention is directed to a polymer composition comprising (preferably consisting of) the following components:

P1. 65 to 100% by weight, preferably 68 to 100% by weight, more preferably 80 to 100% by weight, based on the total polymer composition, of at least one block copolymer P1 comprising at least one vinyl aromatic monomer and at least one diene monomer, wherein the block copolymer P1 comprises
  from 65 to 80% by weight, based on block copolymer P1, of at least one hard block A1 comprising from 90 to 100% by weight, preferably 95 to 100% by weight, based on the total hard block A1, of vinyl aromatic monomers and from 0 to 10% by weight, preferably 0 to 5% by weight, based on the total hard block A1, of diene monomers, and
  from 20 to 35% by weight, based on block copolymer P1, of at least one soft block B1 comprising from 0 to 10% by weight, based on the total soft block B1, of vinyl aromatic monomers, and from 90 to 100% by weight, based on the total soft block B1, of diene monomers;

P2. 0 to 35% by weight, preferably 0 to 32% by weight, more preferably 0 to 20% by weight, based on the total polymer composition, of at least one elastomeric block copolymer P2 comprising at least one vinyl aromatic monomer and at least one diene monomer, wherein the block copolymer P2 comprises
  from 28 to 40% by weight, based on block copolymer P2, of at least one hard block A2 comprising from 90 to 100% by weight, preferably 95 to 100% by weight, based on the total hard block A2, of vinyl aromatic monomers and from 0 to 10% by weight, preferably 0 to 5% by weight, based on the total hard block A2, of diene monomers, and
  from 60 to 72% by weight, based on block copolymer P2, of at least one soft block B2 comprising from 30 to 60% by weight, based on the total soft block B2, of vinyl aromatic monomers, and from 40 to 70% by weight, based on the total soft block B2, of diene monomers;

P3. 0 to 20% by weight, preferably 0 to 10% by weight, based on the total polymer composition, of one or more additional non-elastomeric thermoplastic polymer P3;

C. 0 to 1.5% by weight, preferably 0 to 0.15% by weight, based on the total polymer composition, of at least one demolding additive C;

D. 0 to 10% by weight, preferably 0 to 5% by weight, based on the total polymer composition, of one or more additional additive D, with the proviso that the sum of the components P1 and P3 is equal or more than 75% by weight, preferably equal or more than 75.5% by weight, based on the total polymer composition;

and with the proviso that the composition comprises from 5 to 20% by weight, preferably 6 to 20% by weight, more preferably 6 to 10% by weight, based on the total polymer composition, of component P3 if the amount of component P1 is less than 80% by weight, based on the total composition.

Preferably, the sum of the components P1 and P3 is from 75 to 100% by weight, preferably from 75.5 to 100% by weight, based on the total polymer composition.

In terms of the present invention an "elastomeric polymer" (or also referred to as elastomer) means a polymer that displays rubber-like elasticity. Preferably, an elastomeric polymer exhibits an elasticity modulus (also referred to as tensile modulus) of lower than 500 MPa, preferably lower than 150 MPa (determined according to ISO 527). Also preferably, a elastomeric polymer exhibits a strain at break (determined according to ISO 527) equal or higher than 350%, preferably equal or higher than 400% and/or a Vicat temperature (Vicat A/50 determined according to ISO 306) equal or lower than 65° C., preferably equal or lower than 50° C.

In terms of the present invention, a "non-elastomeric polymer" means a polymer that does not display rubber-like elasticity.

Preferably, a non-elastomeric polymer exhibits an elasticity modulus (also referred to as tensile modulus) of equal or higher than 500 MPa, preferably equal or higher than 1000 MPa (determined according to ISO 527). Also preferably a non-elastomeric polymer exhibits a strain at break (determined according to ISO 527) equal or lower than 10%, preferably equal or lower than 5% and/or a Vicat temperature (Vicat B/50 determined according to ISO 306) equal or higher than 83° C., preferably equal or higher than 100° C.

In the context of the invention "diene" means a conjugated diene.

In the context of the invention ppm (parts per million) means mg/kg and pph (parts per hundred) means 10 g/kg.

In the context of the invention, the average molecular weight MW is determined by gel permeation chromatography (GPC) according to ISO 16014-3:2012 (Low temperature T<60° C. size exclusion with relative calibration method against polystyrene standards in THF).

Typically, the glass transition temperature $T_g$ of the polymer blocks depends on the monomer composition and the 1,2-vinyl amount of diene units. Typically, the glass transition temperature $T_g$ of the polymer blocks can determined using Differential Scanning calorimetry (DSC), Dynamic Mechanical Analysis (DMA) or Differential Thermal Analysis (DTA) or calculated according to Fox Equation. Typically, the glass transition temperature $T_g$ of a hard block (also referred to as hard phase), e.g. of hard blocks A1 and A2, is equal or more than 40° C., preferable equal or more than 50° C. and the glass transition temperature $T_g$ of a soft block (also referred to as soft phase), e.g. of soft blocks B1 and B2, is equal or less than 0° C., preferable equal or less than −30° C.

Preferably, the polymer composition exhibits a melt volume flow rate (MVR), measured on a polymer melt at 200° C. and 5 kg load according to ISO 1133-1:2011, in the range of from 24 to 40 $cm^3$/10 min, preferably 25 to 40 $cm^3$/10 min, more preferably 25 to 38 $cm^3$/10 min, more preferably in the range of from 25.2 to 38 $cm^3$/10 min, more preferably in the range of from 25.2 to 35.2 $cm^3$/10 min.

In another embodiment the inventive polymer composition exhibits a melt volume flow rate (MVR), measured on a polymer melt at 200° C. and 5 kg load according to ISO 1133-1:2011, in the range of 30 to 40 $cm^3$/10 min, more preferably in the range of from 30 to 38 $cm^3$/10 min, also preferably 31 to 36 $cm^3$/10 min, also preferably in the range of from 30.0 to 35.2 $cm^3$/10 min, most preferably in the range of from 31 to 35.2 $cm^3$/10 min.

Preferably, the polymer composition or a molding produced therefrom exhibits a Shore D hardness determined in accordance with ASTM D2240 (measurement after 15 seconds) in the range of from 50 to 68, preferably in the range of 50 to 62, more preferably in the range of from 55 to 62.

Preferably, the polymer composition or a molding produced therefrom exhibits an elasticity modulus (E-modulus), measured according to ISO 527 (e.g. on a Zwick tensile tester with a 2.5 kN+500 N load cell) of more than 1000 MPa, preferably of more than 1020 MPa, more preferably of more than 1050 MPa, in particular of more than 1100 MPa.

Preferably, the inventive polymer composition or a molding produced therefrom exhibits an Vicat temperature, Vicat A/50 measured according to ISO 306:2004, of more than 68° C., preferably of more than 70° C., more preferably of more than 73° C.

In particular, the vinyl aromatic monomer of components P1 and P2 is at least one monomer selected from styrene or substituted styrene. For example one or more substituted styrene according to the following formula (I)

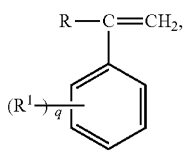

(I)

with

R is hydrogen or $C_1$-$C_8$-alkyl; $R^1$ is hydrogen or $C_1$-$C_8$-alkyl;

with the provision that not both of R and $R^1$ are hydrogen, and q is 1, 2 or 3, preferably 1 or 2;

can be used alone or in combination with unsubstituted styrene as vinyl aromatic monomer in components P1 and P2. Preferably, the at least one vinyl aromatic monomer is selected from styrene, α(alpha)-methylstyrene, and vinyltoluene, more preferably styrene, alpha-methylstyrene or a mixture thereof.

In particular the diene monomer of components P1 and P2 is at least one monomer selected from 1,3-butadiene, isoprene, 1,3-pentadiene and 1-phenylbutadiene. More preferably the diene monomer of components P1 and P2 is 1,3-butadiene.

In a particularly preferred embodiment the vinyl aromatic monomer of components P1 and P2 is styrene and the diene monomer of components P1 and P2 is 1,3-butadiene.

In a preferred embodiment the inventive polymer composition comprises:

P1. 80 to 100% by weight, preferably 82 to 100% by weight, based on the total polymer composition, of the at least one block copolymer P1;

P2. 0 to 20% by weight, preferably 0 to 18% by weight, based on the total polymer composition, of the at least one elastomeric block copolymer P2;

P3. 0 to 20% by weight, preferably 0 to 10% by weight, based on the total polymer composition, of one or more additional non-elastomeric thermoplastic polymer P3, C. 0 to 0.15% by weight, preferably 0.01 to 0.15% by weight, based on the total polymer composition, of the at least one demolding additive C;

D. 0 to 10% by weight, preferably 0 to 5% by weight, more preferably 0 to 2.5% by weight, based on the total polymer composition, of one or more additional additive D.

In another preferred embodiment the inventive polymer composition comprises:

P1. 79.99 to 99.99% by weight, preferably 81.98 to 98.98% by weight, based on the total polymer composition, of the at least one block copolymer P1;

P2. 0 to 20% by weight, preferably 1 to 18% by weight, based on the total polymer composition, of the at least one elastomeric block copolymer P2;

P3. 0 to 10% by weight, preferably 0 to 8% by weight, based on the total polymer composition, of the one or more additional non-elastomeric thermoplastic polymer P3, C. 0.01 to 0.15% by weight, preferably 0.02 to 0.1% by weight, based on the total polymer composition, of the at least one demolding additive C;

D. 0 to 5% by weight, preferably 0 to 2.5% by weight, based on the total polymer composition, of the one or more additional additive D.

Block Copolymer P1

The polymer composition comprises at least 65% by weight, preferably at least 68% by weight, based on the total polymer composition, of the at least one block copolymer P1, comprising (preferably consisting of) at least one vinyl aromatic monomer and at least one diene monomer, wherein the block copolymer P1 comprises (preferably consists of):

from 65 to 80% by weight, based on block copolymer P1, of at least one hard block A1 comprising (preferably consisting of) from 90 to 100% by weight, preferably 95 to 100% by weight, more preferably 98 to 100% by weight, based on the total hard block A1, of vinyl aromatic monomers, in particular styrene, and from 0 to 10% by weight, preferably 0 to 5% by weight, more preferably 0 to 2% by weight, based on the total hard block A1, of diene monomers, in particular 1,3-butadiene, and from 20 to 35% by weight, based on block copolymer P1, of at least one soft block B1 comprising (preferably consisting of) from 0 to 10% by weight, preferably 0 to 5% by weight, based on the total soft block B1, of vinyl aromatic monomers, in particular styrene, and from 90 to 100% by weight, preferably 95 to 100% by weight, based on the total soft block B1, of diene monomers, in particular 1,3-butadiene.

In a preferred embodiment the hard block A1 consists of 100% by weight, based on the hard block A1, of styrene.

In particular the block copolymer P1 is a styrene butadiene block copolymer. Preferably, the block copolymer P1 is a star shaped block copolymer, more preferably a star shaped styrene butadiene block copolymer.

In a preferred embodiment the block copolymer P1 has a melt volume flow rate (MVR), measured according to ISO 1133-1:2011; 200° C./5 kg, in the range of 30 to 40 $cm^3$/min, more preferably in the range of 32 to 38 $cm^3$/min, also preferably in the range of 34 to 36 $cm^3$/min.

In a preferred embodiment the glass transition temperature $T_g$ of the hard block(s) A1 of the block copolymer P1 is above 80° C., and the glass transition temperature $T_g$ of the soft block(s) B1 of the block copolymer P1 is below −60° C., preferably in the range from −60 to −100° C., more preferably −70 to −100° C.

Preferably the at least one soft block B1 of the block copolymer P1 comprises 95 to 100% by weight, preferably 98 to 100% by weight, based on the soft block B1, of the diene monomer, more preferably 1,3-butadiene. More preferably the at least one soft block B1 of the block copolymer P1 essentially consists of diene monomers, preferably 1,3-butadiene.

In particular the molecular weight MW of the soft blocks B1 of the block copolymer P1 is in the range of 8,000 to 40,000 g/mol, preferably in the range of 10,000 to 25,000 g/mol, more preferably in the range of 12,000 to 18,000 g/mol.

Typically, the molecular weight MW given for the block copolymers P1 and P2 and/or the hard and soft blocks (A and B) of block copolymers P1 and P2 is determined by GPC according to ISO 16014-3:2012 (low temperature T<60° C. size exclusion with relative calibration method against polystyrene standards in tetrahydrofuran).

In a preferred embodiment the block copolymer P1 comprises from 20 to 30% by weight, preferably 22 to 27% by weight, based on the total block copolymer P1, of the diene monomers, preferably 1,3-butadiene. Preferably, the block copolymer P1 comprises from 65 to 80% by weight, preferably from 70 to 80% by weight, more preferably 73 to 78% by weight, based on the total block copolymer P1, of the vinyl aromatic monomers, preferably styrene.

Particular preference is given to block copolymers P1 which are star-shaped styrene-butadiene block copolymers comprising at least one of the structures (branches) A1-B1.

Preferably, the block copolymer P1 is a star shaped block copolymer which comprises at least 2 terminal hard blocks A1 consisting of vinyl aromatic monomers, in particular styrene, and comprises one or more soft blocks B1 in each case consisting of 98 to 100% by weight, preferably 100% by weight, of diene, in particular 1,3-butadiene, and from 0 to 2% by weight, of vinyl aromatic monomers, in particular styrene.

Preferably, the proportion by weight of the hard blocks A1 in the block copolymer P1 is from 65 to 80% by weight, preferably from 70 to 80% by weight, more preferably 73 to 78% by weight.

In particular the molecular weight MW of the hard blocks A1 of the block copolymer P1 is in the range of 5,000 to 200,000 g/mol, preferably in the range of 7,000 to 150,000 g/mol, more preferably in the range of 8,000 to 120,000 g/mol.

Preferably, the block copolymer P1 is a star-shaped block copolymer having the structure $[A1\text{-}B1]_nX$; or $[A1\text{-}B1]_nY$; wherein A1 is a vinyl aromatic hard block, B1 is a soft block, X is the radical of an n-functional initiator, Y is the radical of an n-functional coupling agent and n is a natural numbers from 1 to 10, preferably from 3 to 5.

Typically, such block copolymers are obtainable via anionic polymerization of the branches and coupling with an epoxidized vegetable oil, such as epoxidized linseed oil or epoxidized soybean oil. In this instance, a statistical distribution of stars with different amount of branches is produced with most abundant stars having from 2 to 4 branches. The amount and composition of the hard blocks A1 and the soft blocks B1 may be the same or different in the different branches of the star-shaped block copolymer P1.

Preferably, the block copolymer P1 comprises at least 2 terminal hard blocks $A1_1$ and $A1_2$ with different molecular weight, wherein the molecular weight MW of block $A1_1$ is in the range from 35,000 to 200,000 g/mol, preferably in the range of 50,000 to 150,000 g/mol, more preferably in the range of 90,000 to 125,000 g/mol, and wherein molecular weight MW of block $A1_2$ is in the range from 5,000 to 30,000 g/mol, preferably in the range of 6,500 to 20,000 g/mol, more preferably in the range of 7,500 to 15,000 g/mol.

Typically, such block copolymers are obtainable via sequentially anionic polymerization of the branches, wherein the initiator is dosed two times in the corresponding molar ratio and subsequent coupling with a coupling agent, such as epoxidized vegetable oil (e.g. epoxidized linseed oil or epoxidized soybean oil).

Particular preference is given to block copolymers P1, which are star-shaped block copolymers, preferably star-shaped styrene-butadiene block copolymers, having the structure $Y[A1_1\text{-}B1]_m[A1_2\text{-}B1]_l$ or $Y[A1_1\text{-}B1]_m[A1_2\text{-}B1]_l$ wherein $A1_1$ and $A1_2$ are the hard blocks with different molecular weight as described above, B1 is a soft block as described above, Y is the radical of an (m+l)-functional coupling agent and m and l are natural numbers from 1 to 10, preferably 1 to 5. Preferably the ratio of m/l is in the range of 1:2 to 1:5, preferably 1:3 to 1:5. In particular this ratio is a statistical ratio which is obtained by applying this ratio on the molar initiation ratio of both branches during synthesis.

These block copolymers are obtainable via anionic polymerization and coupling with a coupling agent as described by way of example in WO 2008/000623 (Block copolymer A of WO 2008/000623).

Elastomeric Block Copolymer P2

The polymer compositions of the invention can comprise up to 35% by weight, preferably up to 32% by weight, more preferably up to 20% by weight, of the elastomeric block copolymer P2 comprising (preferably consisting of) at least one vinyl aromatic monomer and at least one diene monomer, wherein the block copolymer P2 comprises (preferably consists of):

from 28 to 40% by weight, based on block copolymer P2, of at least one hard block A2 comprising (preferably consisting of) from 90 to 100% by weight, preferably 95 to 100% by weight, based on the total hard block A2, of vinyl aromatic monomers, in particular styrene, and from 0 to 10% by weight, preferably 0 to 5% by weight, based on the total hard block A2, of diene monomers, in particular 1,3-butadiene, and from 60 to 72% by weight, based on block copolymer P2, of at least one soft block B2 comprising (preferably consisting of) from 30 to 60% by weight, preferably 40 to 55% by weight, based on the total soft block B2, of vinyl aromatic monomers, in particular styrene, and from 40 to 70% by weight, preferably 45 to 60% by weight, based on the total soft block B2, of diene monomers, in particular 1,3-butadiene.

In a preferred embodiment, the hard block A2 of the elastomeric block copolymer P2 consists of 100% by weight, based on the hard block A2, of styrene.

Preferably, the soft block B2 of the elastomeric block copolymer P2 can have a random or tapered distribution of the vinyl aromatic monomers and the diene monomers. Also preferably the soft block B2 of the elastomeric block copolymer P2 can consist of multiple sequential blocks B2 (e.g. $B2_1\text{-}B2_2\text{-}B2_3$) with different composition and block lengths.

In particular the elastomeric block copolymer P2 is a thermoplastic elastomer. In particular the elastomeric block copolymer P2 is styrene butadiene block copolymer.

The elastomeric block copolymer P2 may be a star-shaped or linear block copolymer. Preferably, the elastomeric block copolymer P2 is a linear styrene-butadiene block co-polymer, in particular a linear styrene-butadiene block copolymer having properties of a thermoplastic elastomer.

In a preferred embodiment, the glass transition temperature $T_g$ of the hard block(s) A2 of the elastomeric block copolymer P2 is above 50° C., and the glass transition temperature $T_g$ of the soft block(s) B2 of the elastomeric block copolymer P2 is below 0° C.

In a preferred embodiment, the elastomeric block copolymer P2 consists of two or more hard blocks A2 made from vinyl aromatic monomers and one or more random soft blocks B2 consisting of from 30 to 60% by weight, preferably 30 to 55% by weight of vinyl aromatic monomers and from 40 to 70% by weight, preferably from 45 to 70% by weight of dienes. Preferably P2 contains (preferably consists of) the block sequence A2-B2 or A2-B2-A2, where the proportion by weight of the diene in the total block copolymer P2 is from 27 to 46% by weight.

Preferably, the molecular weight MW of at least one hard block A2 of the elastomeric block copolymer P2 is in the range from 5,000 to 100,000 g/mol, more preferably 10,000 to 50,000 g/mol.

In a preferred embodiment, the elastomeric block copolymer P2 has at least one of the following structures:

A2-B2-A2

$X\text{-}[\text{-}B2\text{-}A2]_2$ $Y\text{-}[\text{-}B2\text{-}A2]_m$ $Y[(B2\text{-}A2)_n]_m[A2]_l$ and $Y[(A2\text{-}B2)_nA2]_m[A2]_l$ wherein A2 is one or more vinyl aromatic hard block(s), B2 is one or more soft block(s), X is the radical of an bi-functional initiator, Y is the radical of a m- or (m+l)-functional coupling agent and m, n and l are natural numbers from 1 to 10.

Particular preference is given to linear styrene-butadiene block copolymers P2 of the general structure A2-B2-A2 having, situated between the two A2 blocks, one or more, preferably 1 to 5, more preferably 2 to 4, soft blocks B2 having random styrene/butadiene distribution. These block copolymers are obtainable via anionic polymerization in a non-polar solvent with addition of a polar cosolvent or of a potassium salt, as described by way of example in WO 95/35335 or WO 97/40079 and WO 2010/072596.

The 1,2-vinyl content in the soft blocks B2 of the elastomeric block copolymer P2 is preferably below 20% by weight, in particular in the range from 9 to 15% by weight, particularly preferably in the range from 9 to 12% by weight, based on the total diene content. Suitable block copolymers P2 having such a 1,2-vinyl content in the soft block B2 are described in detail in WO 97/40079. Typically, the vinyl content is the relative proportion of 1,2-linkages of the diene units, based on the entirety of 1,2-, 1,4-cis and 1,4-trans linkages.

In one embodiment, the elastomeric block copolymer P2 has the structure A2-$(B2)_n$-A2, wherein the soft block is composed of more than one soft blocks $(B2)_n$ of different or identical make-up, more preferably identical make-up, with n is a natural number from 2 to 10, preferably 2 to 5, more preferably 2 to 4.

In one embodiment, the elastomeric block copolymer P2 is a linear block copolymer having the structure the structure A2-$(B2)_n$-A2, wherein the vinyl aromatic content of the soft blocks adjacent to the hard A2-blocks is lower than in other soft blocks B2.

In a preferred embodiment, the elastomeric block copolymer P2 is a linear block copolymer of the general structure A2-B2-A2 having, situated between the two A2 blocks, one or more soft blocks B2 having random vinyl aromatic monomer/diene distribution and a 1,2-vinyl content in the copolymer block P2 of below 20%, based on the total diene content.

Preferably, the elastomeric block copolymer P2 comprises (preferably is composed of) 54 to 73% by weight, preferably 60 to 70% by weight, based on the total block copolymer P2, of vinyl aromatic monomers, preferably styrene, and 27 to 46% by weight, preferably 30 to 40% by weight, based on the total block copolymer P2, of diene monomers, preferably 1,3-butadiene.

For example the elastomeric block copolymer P2 is obtainable by anionic polymerization in a non-polar solvent with addition of a polar cosolvent or preferentially of a potassium salt, as described, for example, in WO 96/20248 and WO 97/40079.

Additional Non-Elastomeric Thermoplastic Polymer P3

The polymer compositions of the invention can comprise up to 20% by weight, preferably up to 10% by weight, based on the total polymer composition, of one or more additional non-elastomeric thermoplastic polymers P3, different from P1 and P2.

Based on the present invention the sum of the components P1 and P3 is equal or more than 75% by weight, preferably equal or more than 75.5% by weight, based on the total polymer composition. If the amount of component P1 is less than 80% by weight, based on the total composition, the inventive polymer composition comprises from 5 to 20% by weight, preferably from 6 to 20% by weight, more preferably from 6 to 10% by weight, based on the total polymer composition, of component P3.

The additional non-elastomeric thermoplastic polymer P3 may be any suitable non-elastomeric thermoplastic polymer, for example such as described in WO 96/24634, such as polystyrene, polyamides, polyesters, polyolefins, polyetherketones, polyoxyalkylenes, polyarylene sulfides.

For example the additional non-elastomeric thermoplastic polymer P3 is selected from styrene homo- and/or copolymers, polyamides, polyesters (such as polymethylmethacrylate, PMMA), polyolefins (such as polyethylene and polypropylene), polyether-ketones, polyoxyalkylenes, polyarylene sulfides. Preferably, the additional non-elastomeric polymer P3 is selected from polystyrenes (e.g. such as general purpose polystyrene, GPPS), styrene copolymers, polyamides, polyesters (such as polymethylmethacrylate, PMMA), and polyolefins (such as polyethylene and polypropylene).

In a preferred embodiment the additional non-elastomeric thermoplastic polymer P3 is selected from styrene homo- and/or copolymers, such as general purpose polystyrene (GPPS), high impact polystyrene (HIPS), (meth)acrylate-styrene copolymers, acrylonitrile-styrene copolymers (SAN), acrylonitrile-butadiene-styrene copolymers (ABS), acrylonitrile-styrene-acrylester copolymers (ASA), methacrylate-butadiene-styrene copolymers (MBS) and styrene-butadiene copolymers different from P1 and P2.

Preferably, the additional non-elastomeric thermoplastic polymer P3 may be selected from styrene-butadiene copolymers different from P1 and P2, for example commercial products of type Styrolux®, Styroclear® or K-Resin® (available by INEOS Styrolution).

Preferably, the additional non-elastomeric thermoplastic polymer P3 may be selected from polyolefins, such as homo and copolymers of ethylene, propylene, 1-butene, 1-pentene, 1-hexene, 1-heptene, 3-methyl-1-butene-1,4-methyl-1-butene, 4-methyl-1-pentene, and 1-octene. In particular the polyolefin may be selected from high-density-polyethylene (HDPE), low-density polyethylene (LDPE), linear-low-density polyethylene (LLDPE), polypropylene, or ethylene-propylene copolymers.

More preferably, the additional non-elastomeric thermoplastic polymer P3 is selected from general purpose polystyrene (GPPS).

The preparation, structure and properties of general purpose polystyrene (GPPS) are for example described in detail in the review literature (Kunststoffhandbuch, Vol. 4, Polystyrol, Carl Hanser Verlag, 1996).

Preferably, the additional non-elastomeric thermoplastic polymer P3 is selected from general purpose polystyrene (GPPS) having a molecular weight MW in the range of from 100,000 to 320,000 g/mol, preferably in the range of from 120,000 to 220,000 g/mol. Typically, the polydispersity index D ($M_w/M_n$) of the general purpose polystyrene used as P3 is in the range of 2 to 5, preferably 2.2 to 4.5. Typically, the molecular weight MW and the polydispersity index D are determined by gel permeation chromatography (GPC) according to ISO 16014-3:2012 (Low temperature T<60° C. size exclusion with relative calibration method against polystyrene standards in THF).

Preferably, the additional non-elastomeric thermoplastic polymer P3 is selected from general purpose polystyrene (GPPS) having a melt volume flow rate (MVR), measured on a polymer melt at 200° C. and 5 kg load according to ISO 1133-1:2011, in the range of from 8 to 35 $cm^3$/10 min, preferably 10 to 30 $cm^3$/10 min. Preferably, the additional non-elastomeric thermoplastic polymer P3 is selected from general purpose polystyrene (GPPS) having a Vicat temperature, Vicat B/50 measured according to ISO 306:2004, in the range of from 80 to 110° C., preferably 85 to 105° C.

Suitable general purpose polystyrene is prepared by the anionic or free-radical polymerization process. The polymer's inhomogeneity, which can be affected by the polymerization process, is of subordinate significance here.

Preferably, the polymer composition comprises from 0.5 to 20% by weight, preferably 1 to 10% by weight, more preferably 2 to 8% by weight, based on the total polymer composition, of one or more general purpose polystyrene as component P3.

In a preferred embodiment the polymer composition comprises from 6 to 20% by weight, preferably 6 to 10% by weight, based on the total polymer composition, of one or more general purpose polystyrene as component P3, if the amount of component P1 is less than 80% by weight, based on the total composition, the inventive polymer composition.

Demolding Additive C.

The inventive polymer composition can comprise up to 1.5% by weight, preferably up to 0.15% by weight, more preferably up to 0.1% by weight, based on the total polymer composition, of one or more demolding additive C.

The demolding additive C can be selected from commonly known mold-release agents and lubricants used in styrene polymer compositions, in particular selected from known waxes and oils.

Preferably, the demolding additive C is selected from long-chain fatty acids, such as stearic acid or behenic acid, salts of fatty acids (e.g. calcium stearate or zinc stearate), esters of fatty acids (e.g. stearyl stearate or pentaerythritol tetrastearate), amide derivatives of fatty acids (e.g. ethylenebisstearylamide, erucamide, Acrawax®), phosphates (such as tricalcium phosphate), hydrocarbon waxes, such as microcrystalline waxes and paraffin waxes (e.g. Besquare®), and fumed silica (e.g. Aerosil®). Typically fatty acids are carboxylic acids having a linear or branched, saturated or unsaturated $C_5$-$C_{25}$ alkyl chain.

More preferably, the demolding additive C is selected from stearic acid, stearates, stearic acid esters and stearic acid amides. Most preferably the at least demolding agent C is selected from stearic acid and stearates, such as calcium stearate and zinc stearate.

In a preferred embodiment, the polymer composition comprises from 0.01 to 0.15% by weight, preferably 0.02 to 0.10% by weight, based on the total polymer composition, of at least one demolding additive C, preferably selected from fatty acids, esters of fatty acids, amide derivatives of fatty acids and hydrocarbon waxes, more preferably selected from stearic acid, stearates, stearic acid esters and stearic acid amides.

Additional Additive D

The inventive polymer composition may comprise up to 10% by weight, preferably up to 5% by weight, based on the total polymer composition, of one or more additional additive D, which is different from C. Preferably, the polymer composition may comprise from 0.01 to 10% by weight, preferably 0.1 to 5, more preferably 0.1 to 2.5% by weight, of one or more additives D.

The additional additive is typically selected from commonly known additives for styrene butadiene copolymers and compositions thereof.

The polymer compositions may comprise, as component D, from 0.01 to 5% by weight of usual additives different from demolding agent C, such as processing aids, stabilizers, oxidation inhibitors, ultra-violet light absorbers, flame retardants, colorants, pigments, and plasticizers.

Examples of oxidation inhibitors and heat stabilizers are sterically hindered phenols, various substituted representatives of these groups and mixtures thereof in concentrations of up to 1% by weight, based on the weight of the total polymer composition.

UV stabilizers which may be mentioned, and are generally used in amounts of up to 2% by weight, based on the total polymer composition, are various substituted resorcinols, salicylates, benzotriazoles and benzophenones.

Preferred is the use of a stabilizer, in particular oxygen radical scavengers such as Irganox® 1010 (BASF SE), Songnox® 1010, Irganox® 1076, Irganox® 565 and blends thereof, carbon radical scavengers such as Sumilizer® GS, Sumilizer® GM and blends thereof, and/or secondary stabilizers such as Irgafos® 168 (BASF SE). Said stabilizers are commercially available. The afore-mentioned stabilizers are preferably used in amounts of 0.01 to 0.5 wt.-%, more preferably 0.1 to 0.3 wt.-%.

An example of a processing aid, which can be used in amounts from 0.1 to 5% by weight, preferably from 0.5 to 3% by weight, is a homogeneously miscible oil or oil mixture, in particular selected from mineral oils (medical grade mineral oil), vegetable oils (also referred to as plant oils) and silicon oils.

Preferably, the additives used in the inventive polymer composition as additional additive D are not scattering light in order to maintain transparency of the polymer composition.

Process for Preparing the Inventive Polymer Composition

The present invention also is directed to a process for the preparation of the polymer compositions. In particular the invention is directed to a process for the preparation of the polymer compositions as described above, wherein the components P1 and optionally P2, P3, C and/or D are melt compounded at a temperature in the range of 180 to 280° C., preferably 200 to 250° C.

The inventive polymer compositions may be prepared by processes known per se. For example extruders, such a co-rotating or counter rotating single- or twin screw extruders, or other conventional kneading apparatuses, such as continuous or batch kneaders, Brabender mixers or Banbury mixers, may be used for the preparation of the polymer composition. Said kneading elements should ensure sufficient homogenization of the components guaranteeing micromixing.

The polymer composition may be obtained by mixing and homogenization the components by the usual methods of plastic technology, wherein the sequence of adding the components may be varied.

Moldings Made of the Polymer Compositions

Further, the present invention is directed to moldings (shaped articles) made from the polymer compositions as described above. In particular the moldings may be prepared by commonly known injection molding processes.

In particular the molding made of the inventive polymer composition is a medical device, in particular a transparent, elastic and flexible device, such as a container, a tube, a hose, or bag, e.g. for perfusion or transfusion systems, infusion instruments, dialysis units.

In a preferred embodiment the invention is directed to a molding made of the inventive polymer composition as described above, wherein the molding is a medical device, preferably a drip chamber.

In particular the molding, preferably the medical device, more preferably the drip chamber, exhibits one or more, preferably all, of the following properties:

Melt volume flow rate (MVR), measured on a polymer melt at 200° C. and 5 kg load according to ISO 1133-1:2011, in the range of from 24 to 40 $cm^3$/10 min, preferably in the range of from 25 to 40 $cm^3$/10 min, more preferably in the range of from 25 to 38 $cm^3$/10 min, also preferably in the range of from 25.2 to 38 $cm^3$/10 min, most preferably in the range of from 25.2 to 35.2 $cm^3$/10 min;

Shore D hardness determined in accordance with ASTM D2240 (measurement after 15 seconds) in the range of from 50 to 68, preferably in the range of 50 to 62, more preferably in the range of from 55 to 62;

Elasticity modulus (E-modulus), measured according to ISO 527 (e.g. on a Zwick tensile tester with a 2.5 kN+500 N load cell) of more than 1000 MPa, preferably of more than 1020 MPa, more preferably of more than 1050 MPa, in particular of more than 1100 MPa;

Vicat temperature, Vicat A/50 measured according to ISO 306:2004, of more than 68° C., preferably of more than 70° C., more preferably of more than 73° C.

In a preferred embodiment the molding is a medical device, in particular a transparent, soft and flexible medical device. In an especially preferred embodiment the inventive molding is a drip chamber.

Use of the Polymer Composition

Further, the present invention is directed to the use of the inventive polymer composition as described above for preparing a molding. The polymer compositions of the invention can advantageously be used for the preparation of transparent, soft and flexible medical devices, such as medical tubes, medical hoses, medical bags, medical foils, catheters, balloons and drip chambers.

Preferably, the invention is directed to the use of the inventive polymer composition as described above for preparing a molding, wherein the molding is a medical device, preferably a drip chamber. More preferably, the polymer compositions of the invention are optimized for the production of drip chambers, in particular drip chambers having one or more of the properties as defined above.

The following examples and the claims further describe the invention:

EXAMPLES

1. Test Methods a. Melt Volume Flow Rate (MVR): MVR measured on a polymer melt at 200° C. and 5 kg load according to ISO 1133-1:2011.

b. Mechanical properties: Specimen for Shore D, tensile test and Vicat were produced via injection molding at 220° C., a screw rotational speed of 500 mm/s, injection speed of 100 mm/s, injection pressure of 1500 bar and cooling time of 50 s at 25° C.

Subsequently, the specimens were conditioned at for 24 h at 23° C.

The Shore D hardness values (measurement after 15 seconds) were measured using a measuring column and an analogue Shore D meter according to ASTM D2240 from BAQ GmbH (Germany). The measurements were taken on the surface of a plate with a minimum thickness of 6 mm (or 2 plates of 3 mm on top of each other). The value given is the average value over 10 measurements.

Tensile tests (stress and strain at yield and at break as well as E-modulus) were measured on a Zwick tensile tester (with a 2.5 kN+500 N load cell) according to ISO 527. For this, samples were prepared according to the 1 A shape specified in the standard. The value given is the average value over minimal 5 measurements.

The Vicat Temperature (Vicat A/50) using 1 kg was determined according to ISO306:2004.

c. Demolding Behavior

The molding behavior was evaluated during production of the 1A test specimen used for tensile test. The demolding behavior was described with numbers 1-4:

1: Very good demolding
2: Average demolding
3: Bad demolding
4: Very bad demolding

2. Preparation of Polymer Compositions and Test Specimens

The following components are used:

Block Copolymer P1:

P1: Star shaped styrene-butadiene block copolymer P1 with amount of butadiene in the total block copolymer is 25% by weight and that of styrene is 75% by weight (both based on total monomer), MVR (200° C./5 kg) is 34 $cm^3$/10 min.

The block copolymer P1 was prepared as described in the following:

In a batch reactor (stainless steel reactor, stirred, 50 $m^3$) 20000 L of cyclohexane at 40° C. was used as initial charge and 3885 L styrene (S1) was added at 20 $m^3$/h. When 388 L of S1 had been dosed, 26.00 L of a 1.4 M sec-butyllithium solution (BuLi 1) for initiation had been dosed at once. The reaction was allowed to proceed under continuous stirring to complete monomer consumption (identified by no further temperature increase of the reaction mixture). After complete monomer consumption, the polymerization mixture was cooled by means of reflux cooling to a temperature below 60° C.

Next, 114.40 L of a 1.4 M sec-butyllithium (BuLi 2) solution was added at once, as the second initiator mixture.

In a next step, again 2147 L styrene (S2) was added and the polymerization reaction, under continuous stirring, was allowed to run to complete monomer consumption (identified by no further temperature increase of the reaction mixture). After complete monomer consumption, the polymerization mixture was cooled by means of reflux cooling to a temperature below 50° C.

Then, 2951 L butadiene (B1) was added and the polymerization reaction, under continuous stirring, was allowed to run to complete monomer consumption (identified by no further temperature increase of the reaction mixture).

Then, 10 minutes after the last complete monomer consumption, 18.8 L Efka® PL 5382 (epoxidized soya bean oil, BASF), heated to a temperature of 85° C., as coupling agent was added to the polymer solution and allowed to react for 10 minutes while stirring.

The reaction mixture was stabilized by acidification with 0.05 phm* demineralized water and a 0.36 phm $CO_2$ gas stream and stabilized with 0.15 phm Sumilizer® GS, 0.20 phm Irganox01010 and 0.15 phm Irgaphos® 168 in a continuous fashion using a static mixer.

*phm=per hundred parts by weight of monomer', meaning wt.-% of component (initiator, coupling agent etc.) is calculated on the total mass of the monomers)

Finally, the cyclohexane solvent was removed by means of a flash evaporization followed by a degassing extruder and under-water pelletization to obtain the styrene-butadiene block copolymer granulate.

Elastomeric Block Copolymer P2:

P2: Linear styrene-butadiene block copolymer P2 with amount of butadiene in the total block copolymer is 35% by weight and that of styrene is 65% by weight (both based on total monomer), MVR (200° C./5 kg) is 14 cm3/10 min.

The block copolymer P2 was prepared as described in the following:

In a batch reactor (stainless steel reactor, stirred, 50 $m^3$) 20500 L of cyclohexane at 40° C. was used as initial charge and 1344 L styrene (S1) was added at 20 $m^3$/h. When 134 L of S1 had been dosed, 47.91 L of a 1.4 M sec-butyllithium solution (BuLi 1) for initiation and 6.23 L of a 5 wt.-% potassium tert-amylate solution in cyclohexane as randomizer had been dosed at once. The reaction was allowed to proceed under continuous stirring to complete monomer consumption (identified by no further temperature increase of the reaction mixture). After complete monomer consumption, the polymerization mixture was cooled by means of reflux cooling to a temperature below 65° C.

In a next step, 924 L styrene (S2) and 1439 L butadiene (B1) were added together and the polymerization reaction, under continuous stirring, was allowed to run to complete monomer consumption (identified by no further temperature increase of the reaction mixture). After complete monomer consumption, the polymerization mixture was cooled by means of reflux cooling to a temperature below 48° C.

In a next step, 1193 L styrene (S3) and 1857 L butadiene (B2) were added together and the polymerization reaction, under continuous stirring, was allowed to run to complete monomer consumption (identified by no further temperature increase of the reaction mixture). After complete monomer consumption, the polymerization mixture was cooled by means of reflux cooling to a temperature below 65° C.

In a next step, 655 L styrene (S4) and 1020 L butadiene (B3) were added together and the polymerization reaction, under continuous stirring, was allowed to run to complete monomer consumption (identified by no further temperature increase of the reaction mixture). After complete monomer consumption, the polymerization mixture was cooled by means of reflux cooling to a temperature below 65° C.

In a next step, 1344 L styrene (S5) was added and the polymerization reaction, under continuous stirring, was allowed to run to complete monomer consumption (identified by no further temperature increase of the reaction mixture).

Then, 10 minutes after the last complete monomer consumption, 9.8 L isopropanol was added to the polymer solution and allowed to react for 10 minutes while stirring.

Then, the reaction mixture was stabilized by acidification with 0.06 phm* demineralized water and a 0.43 phm $CO_2$ gas stream and stabilized with 0.15 phm Sumilizer® GS, 0.20 phm Irganox® 1010 and 0.15 phm Irgaphos® 168 in a continuous fashion using a static mixer.

*phm=per hundred parts by weight of monomer' (wt.-% of component (initiator, coupling agent etc.) is calculated on the total mass of the monomers).

Finally, the cyclohexane solvent was removed by means of a flash evaporization followed by a degassing extruder and under-water pelletization to obtain the styrene-butadiene block copolymer granulate.

Additional Non-Elastomeric Thermoplastic Polymer P3:

P3_I: General purpose polystyrene 124N (from INEOS Styrolution, Germany) with a melt volume flow rate MVR of 12 $cm^3$/10 min (200° C./5 kg) and Vicat B/50 87° C.

P3_II: General purpose polystyrene 156F (from INEOS Styrolution, Germany) with a melt volume flow rate MVR of 28 $cm^3$/10 min (200° C./5 kg) and Vicat B/50 101° C.

Additive C

C: Master batch comprising 5% zinc stearate

Polymer compositions as summarized in Table 1 were made by melt compounding on a twin screw extruder at mass temperatures of 230° C.

Specimens were prepared by injection molding as described above.

TABLE 1

Composition of polymer compositions, values are given as % by weight, based on the total polymer composition, pph is calculated based on zinc stearate and means parts zinc stearate per hundred parts of P1 + P2 + P3, Comp = comparative example, Inv = inventive example

| | | | | | | C | | |
|---|---|---|---|---|---|---|---|---|
| Ex. | | P1 % | P2 % | P3_I % | P3_II % | % | pph based on P1 + P2 + P3 | P1 + P3 % |
| 1 | Comp | 78.82 | 19.70 | — | — | 1.48 | 0.075 | 78.82 |
| 2 | Comp | 73.89 | 24.63 | — | — | 1.48 | 0.075 | 73.89 |
| 3 | Comp | 68.97 | 29.56 | — | — | 1.48 | 0.075 | 68.97 |
| 4 | Comp | 73.53 | 24.51 | — | — | 1.96 | 0.100 | 73.53 |
| 5 | Comp | 72.41 | 24.14 | 1.97 | — | 1.48 | 0.075 | 74.38 |
| 6 | Inv | 69.70 | 23.23 | 5.59 | — | 1.48 | 0.075 | 75.29 |
| 7 | Inv | 68.41 | 22.80 | 7.31 | — | 1.48 | 0.075 | 75.72 |
| 8 | Comp | 74.26 | 24.75 | — | — | 0.99 | 0.05 | 74.26 |
| 9 | Inv | 84.16 | 14.85 | — | — | 0.99 | 0.05 | 84.16 |
| 10 | Inv | 89.11 | 9.90 | — | — | 0.99 | 0.05 | 89.11 |
| 11 | Inv | 94.06 | 4.95 | — | — | 0.99 | 0.05 | 94.06 |
| 12 | Inv | 99.01 | — | — | — | 0.99 | 0.05 | 99.01 |
| 13 | Inv | 84.06 | 9.34 | — | 5.61 | 0.99 | 0.05 | 89.67 |
| 14 | Inv | 69.70 | 23.23 | — | 5.59 | 1.48 | 0.075 | 75.29 |
| 15 | Inv | 100.00 | — | — | — | — | — | 100.00 |

3. Results

The test results for polymer compositions according to examples 1 to 15 were obtained as described above.

The results are summarized in Table 2.

TABLE 2

Test results

| Ex. Unit Target value | | MVR $cm^3$/10 min 24-40 | Vicat A/50 ° C. >68 | Hardness Shore D =<62 | Stress at yield MPa | Strain at yield % | Stress at break MPa | Strain at break % | modulus MPa >1000 |
|---|---|---|---|---|---|---|---|---|---|
| 1 | Comp | 26.0 | 69.2 | 54.9 | 15.3 | 1.9 | 17.0 | 250 | 973 |
| 2 | Comp | 24.0 | 65.7 | 51.4 | 13.4 | 1.9 | 17.4 | 256 | 869 |
| 3 | Comp | 22.7 | 62.1 | 50.6 | 12.3 | 1.8 | 16.5 | 279 | 822 |
| 4 | Comp | 25.4 | 66.2 | 52.8 | 13.4 | 1.8 | 17.3 | 269 | 883 |
| 5 | Comp | 25.0 | 66.7 | 52.1 | 14.0 | 1.8 | 17.3 | 252 | 918 |
| 6 | Inv | 24.3 | 68.8 | 55.8 | 15.6 | 1.8 | 17.8 | 236 | 1020 |

TABLE 2-continued

| Test results | | | | | | | | | | |
|---|---|---|---|---|---|---|---|---|---|---|
| Ex. Unit Target value | | MVR $cm^3$/10 min 24-40 | Vicat A/50 ° C. >68 | Hardness Shore D =<62 | Stress at yield MPa | Strain at yield % | Stress at break MPa | Strain at break % | modulus MPa >1000 |
| 7 | Inv | 25.4 | 70.5 | 56.2 | 16.1 | 1.8 | 17.5 | 219 | 1070 |
| 8 | Comp | 25.0 | 66.4 | 51.9 | 13.8 | 1.8 | 16.7 | 251 | 907 |
| 9 | Inv | 30.2 | 73.3 | 58.0 | 17.0 | 1.9 | 18.2 | 242 | 1040 |
| 10 | Inv | 32.1 | 74.2 | 60.0 | 19.0 | 1.9 | 18.2 | 227 | 1130 |
| 11 | Inv | 35.0 | 76.6 | 61.0 | 21.0 | 1.9 | 18.2 | 222 | 1270 |
| 12 | Inv | 35.0 | 79.8 | 62.0 | 25.0 | 1.9 | 16.9 | 177 | 1430 |
| 13 | Inv | 32.2 | 77.0 | 62.0 | 21.0 | 1.9 | 17.8 | 182 | 1290 |
| 14 | Inv | 24.3 | 69.4 | 56.0 | 15.0 | 1.8 | 18.0 | 236 | 1000 |
| 15 | Inv | 34.1 | 79.5 | 60.0 | 24.0 | 2.0 | 16.5 | 174 | 1390 |

The results show that the inventive polymer compositions are within the target values which are in particular required for the production of medical drip chambers.

It was found that the desired balance of properties, in view of melt flow rate, heat stability, hardness and elasticity, can be achieved if the amount of the defined block copolymer P1 is at least 65% by weight, the sum of the non-elastomeric polymeric components P1 and P3 is at least 75% by weight, and the composition comprises from 6 to 20% by weight of component P3 if the amount of component P1 is less than 80% by weight.

The desired balance of properties is also obtained if the amount of the defined block copolymer P1 is at least 80% by weight, preferably at least 81% by weight, the amount of the elastomeric block copolymer P2 is up to 20% by weight, preferably up to 19% by weight, and the other components are within the claimed ranges.

The invention claimed is:

1. A polymer composition comprising the following components:

P1. 65 to 99% by weight, based on the total polymer composition, of at least one block copolymer P1 comprising at least one vinyl aromatic monomer and at least one diene monomer, wherein the block copolymer P1 comprises:

from 65 to 80% by weight, based on block copolymer P1, of at least one hard block A1 comprising from 90 to 100% by weight, based on the total hard block A1, of vinyl aromatic monomers and from 0 to 10% by weight, based on the total hard block A1, of diene monomers, and from 20 to 35% by weight, based on block copolymer P1, of at least one soft block B1 comprising from 0 to 10% by weight, based on the total soft block B1, of vinyl aromatic monomers and from 90 to 100% by weight, based on the total soft block B1, of diene monomers;

P2. 1 to 35% by weight, based on the total polymer composition, of at least one elastomeric block copolymer P2 comprising at least one vinyl aromatic monomer and at least one diene monomer, wherein the block copolymer P2 comprises:

from 28 to 40% by weight, based on block copolymer P2, of at least one hard block A2 comprising from 90 to 100% by weight, based on the total hard block A2, of vinyl aromatic monomers and from 0 to 10% by weight, based on the total hard block A2, of diene monomers, and from 60 to 72% by weight, based on block copolymer P2, of at least one soft block B2 comprising from 30 to 60% by weight, based on the total soft block B2, of vinyl aromatic monomers, and from 40 to 70% by weight, based on the total soft block B2, of diene monomers;

P3. 0 to 20% by weight, based on the total polymer composition, of one or more additional non-elastomeric thermoplastic polymer P3;

C. 0 to 1.5% by weight, based on the total polymer composition, of at least one demolding additive C; and D. 0 to 10% by weight, based on the total polymer composition, of one or more additional additive D;

with the proviso that the sum of the components P1 and P3 is equal or more than 75% by weight, based on the total polymer composition, and with the proviso that the composition comprises from 5 to 20% by weight, based on the total polymer composition, of component P3 if the amount of component P1 is less than 80% by weight, based on the total composition, wherein the polymer composition exhibits a melt volume flow rate (MVR), measured on a polymer melt at 200° C. and 5 kg load according to ISO 1133-1:2011, in the range of from 24 to 40 $cm^3$/10 min, and the block copolymer P1 has a melt volume flow rate (MVR), measured according to ISO 1133-1:2011; 200° C./5 kg, in the range of 30 to 40 $cm^3$/10 min.

2. The polymer composition according to claim 1, wherein the polymer composition comprises:

P1. 80 to 99% by weight, based on the total polymer composition, of at least one block copolymer P1;

P2. 1 to 20% by weight, based on the total polymer composition, of at least one elastomeric block copolymer P2;

P3. 0 to 20% by weight, based on the total polymer composition, of one or more additional non-elastomeric thermoplastic polymer P3;

C. 0 to 0.15% by weight, based on the total polymer composition, of at least one demolding additive C; and D. 0 to 10% by weight, based on the total polymer composition, of one or more additional additive D.

3. The polymer composition according to claim 1, wherein the block copolymer P1 comprises from 20 to 30% by weight, based on the total block copolymer P1, of the diene monomer.

4. The polymer composition according to claim 1, wherein the glass transition temperature $T_g$ of the hard block(s) A1 of the block copolymer P1 is above 80° C., and the glass transition temperature $T_g$ of the soft block(s) B1 of the block copolymer P1 is below −60° C.

5. The polymer composition according to claim 1, wherein the elastomeric block copolymer P2 comprises from 30 to 40% by weight, based on the total block copolymer P2, of the diene monomer.

6. The polymer composition according to claim 1, wherein the glass transition temperature $T_g$ of the hard block(s) A2 of the elastomeric block copolymer P2 is above 50° C., and the glass transition temperature $T_g$ of the soft block(s) B2 of the elastomeric block copolymer P2 is below 0° C.

7. The polymer composition according to claim 1, wherein the additional non-elastomeric thermoplastic polymer P3 is selected from polystyrenes, styrene copolymers, polyamides, polyesters, and polyolefins.

8. The polymer composition according to claim 1, wherein the polymer composition comprises from 1 to 10% by weight, based on the total polymer composition, of one or more additional non-elastomeric thermoplastic polymer P3 selected from polystyrenes.

9. The polymer composition according to claim 1, wherein the polymer composition comprises from 0.01 to 0.15% by weight, based on the total polymer composition, of the at least one demolding additive C selected from stearic acid, stearates, stearic acid esters, and stearic acid amides.

10. The process for the preparation of a polymer composition according to claim 1, wherein the component P1 and P2 and optionally P3, C, and/or D are melt compounded at a temperature in the range 180 to 280° C.

11. A molding made from the polymer composition comprising the following components:

P1. 65 to 99% by weight, based on the total polymer composition, of at least one block copolymer P1 comprising at least one vinyl aromatic monomer and at least one diene monomer, wherein the block copolymer P1 comprises:

from 65 to 80% by weight, based on block copolymer P1, of at least one hard block A1 comprising from 90 to 100% by weight, based on the total hard block A1, of vinyl aromatic monomers and from 0 to 10% by weight, based on the total hard block A1, of diene monomers, and from 20 to 35% by weight, based on block copolymer P1, of at least one soft block B1 comprising from 0 to 10% by weight, based on the total soft block B1, of vinyl aromatic monomers and from 90 to 100% by weight, based on the total soft block B1, of diene monomers;

P2. 1 to 35% by weight, based on the total polymer composition, of at least one elastomeric block copolymer P2 comprising at least one vinyl aromatic monomer and at least one diene monomer, wherein the block copolymer P2 comprises:

from 28 to 40% by weight, based on block copolymer P2, of at least one hard block A2 comprising from 90 to 100% by weight, based on the total hard block A2, of vinyl aromatic monomers and from 0 to 10% by weight, based on the total hard block A2, of diene monomers, and from 60 to 72% by weight, based on block copolymer P2, of at least one soft block B2 comprising from 30 to 60% by weight, based on the total soft block B2, of vinyl aromatic monomers, and from 40 to 70% by weight, based on the total soft block B2, of diene monomers;

P3. 0 to 20% by weight, based on the total polymer composition, of one or more additional non-elastomeric thermoplastic polymer P3;

C. 0 to 1.5% by weight, based on the total polymer composition, of at least one demolding additive C; and D. 0 to 10% by weight, based on the total polymer composition, of one or more additional additive D;

with the proviso that the sum of the components P1 and P3 is equal or more than 75% by weight, based on the total polymer composition;

and with the proviso that the composition comprises from 5 to 20% by weight, based on the total polymer composition, of component P3 if the amount of component P1 is less than 80% by weight, based on the total composition, wherein the polymer composition exhibits a melt volume flow rate (MVR), measured on a polymer melt at 200° C. and 5 kg load according to ISO 1133-1:2011, in the range of from 24 to 40 $cm^3$/10 min, and the block copolymer P1 has a melt volume flow rate (MVR), measured according to ISO 1133-1:2011; 200° C./5 kg, in the range of 30 to 40 $cm^3$/10 min, and wherein the molding is a medical device.

12. The molding according to claim 11, wherein the molding is a drip chamber.

13. A method for preparing a molding, wherein the molding is a medical device made from a polymer composition comprising the following components:

P1. 65 to 99% by weight, based on the total polymer composition, of at least one block copolymer P1 comprising at least one vinyl aromatic monomer and at least one diene monomer, wherein the block copolymer P1 comprises:

from 65 to 80% by weight, based on block copolymer P1, of at least one hard block A1 comprising from 90 to 100% by weight, based on the total hard block A1, of vinyl aromatic monomers and from 0 to 10% by weight, based on the total hard block A1, of diene monomers, and from 20 to 35% by weight, based on block copolymer P1, of at least one soft block B1 comprising from 0 to 10% by weight, based on the total soft block B1, of vinyl aromatic monomers and from 90 to 100% by weight, based on the total soft block B1, of diene monomers;

P2. 1 to 35% by weight, based on the total polymer composition, of at least one elastomeric block copolymer P2 comprising at least one vinyl aromatic monomer and at least one diene monomer, wherein the block copolymer P2 comprises:

from 28 to 40% by weight, based on block copolymer P2, of at least one hard block A2 comprising from 90 to 100% by weight, based on the total hard block A2, of vinyl aromatic monomers and from 0 to 10% by weight, based on the total hard block A2, of diene monomers, and from 60 to 72% by weight, based on block copolymer P2, of at least one soft block B2 comprising from 30 to 60% by weight, based on the total soft block B2, of vinyl aromatic monomers, and from 40 to 70% by weight, based on the total soft block B2, of diene monomers;

P3. 0 to 20% by weight, based on the total polymer composition, of one or more additional non-elastomeric thermoplastic polymer P3;

C. 0 to 1.5% by weight, based on the total polymer composition, of at least one demolding additive C; and D. 0 to 10% by weight, based on the total polymer composition, of one or more additional additive D, with the proviso that the sum of the components P1 and P3 is equal or more than 75% by weight, based on the total polymer composition;

and with the proviso that the composition comprises from 5 to 20% by weight, based on the total polymer composition, of component P3 if the amount of component P1 is less than 80% by weight, based on the total composition;

wherein the polymer composition exhibits a melt volume flow rate (MVR), measured on a polymer melt at 200° C. and 5 kg load according to ISO 1133-1:2011, in the range of from 24 to 40 $cm^3$/10 min, and the block copolymer P1 has a melt volume flow rate (MVR), measured according to ISO 1133-1:2011; 200° C./5 kg, in the range of 30 to 40 $cm^3$/10 min, and wherein the method comprises injection molding of the polymer composition.

14. The method according to claim 13, wherein the molding is a drip chamber.

* * * * *